(12) United States Patent
Purpura et al.

(10) Patent No.: US 8,470,546 B2
(45) Date of Patent: Jun. 25, 2013

(54) TREATMENT OF AUTISM SPECTRUM DISORDERS WITH AGENTS THAT ACTIVATE THE LOCUS COERULEUS-NORADRENERGIC SYSTEM

(75) Inventors: Dominick P. Purpura, New York, NY (US); Mark F. Mehler, Riverdale, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 743 days.

(21) Appl. No.: 12/589,854

(22) Filed: Oct. 29, 2009

(65) Prior Publication Data
US 2010/0130566 A1   May 27, 2010

Related U.S. Application Data

(60) Provisional application No. 61/200,216, filed on Nov. 25, 2008.

(51) Int. Cl.
*G01N 33/74* (2006.01)
(52) U.S. Cl.
USPC .................... 435/7.21; 514/17.5; 514/18.1
(58) Field of Classification Search
None
See application file for complete search history.

(56) References Cited

PUBLICATIONS

Aman M G et al., entitled "Pharmacotherapy for Hyperactivity in Children with Autism and Other Pervasive Developmental Disorders,".Journal of Autism and Developmental Disorders, vol. 30, No. 5, 2000, 451-459.
Curran L K et al., entitled "Behaviors Associated With Fever in Children With Autism Spectrum Disorders," Pediatrics, vol. 120, No. 6, Dec. 2007, e1386-e1392.
Erickson C A et al., entitled "Pharmacologic Treatment of Autism and Related Disorders," Pediatric Annals 36:9, Sep. 2007, 575-585.
Fankhauser M P et al., entitled "A double-blind, placebo-controlled study of the efficacy of transdermal clonidine in autism," J Clin Psychiatry, Mar. 1992;53(3):77-82, Abstract Only.
Handen B L et al., entitled Guanfacine in children with autism and/or intellectual disabilities, J Dev Behav Pediatr, Aug. 2008;29(4):303-8, Abstract Only.
Mehler M F et al., entitled "Autism, fever, epigenetics and the locus coeruleus," Brain Res Rev, Mar. 2009;59(2):388-92, Epub Nov. 24, 2008, Abstract Only.
Minderaa R B et al., entitled "Noradrenergic and Adrenergic Functioning in Autism," Biol Psychiatry, 1994;36:237-241.
Ming X et al., entitled "Use of clonidine in children with autism spectrum disorders," Brain Dev, Aug. 2008;30(7):454-60, Abstract Only.
Myers S M et al., entitled "The status of pharmacotherapy for autism spectrum disorders," Expert Opin Pharmacother, 2007,8(11) 1579-1603.
Mehler M F et al., entitled "Autism, fever, epigenetics and the locus coeruleus," Brain Res Rev., Mar. 2009; 59(2): 388-392.

*Primary Examiner* — Robert C Hayes
(74) *Attorney, Agent, or Firm* — Amster, Rothstein & Ebenstein LLP

(57) ABSTRACT

Methods are provided for treating autism spectrum disorders (ASD) using agents that activate the locus coeruleus-noradrenergic (LC-NA) system of the brain and for screening for compounds for treating ASD comprising determining whether or not the compounds activate the LC-NA system.

6 Claims, No Drawings

TREATMENT OF AUTISM SPECTRUM DISORDERS WITH AGENTS THAT ACTIVATE THE LOCUS COERULEUS-NORADRENERGIC SYSTEM

CROSS-REFERENCE TO RELATED APPLICATION

This application claims the benefit of U.S. Provisional Patent Application No. 61/200,216, filed Nov. 25, 2008, the content of which is incorporated by reference.

STATEMENT OF GOVERNMENT SUPPORT

This invention was made with government support under grant numbers RO1 MH66290 and RO1 NS38902 awarded by the National Institutes of Health. The government has certain rights in the invention.

FIELD OF THE INVENTION

The present invention relates to treatment of autism spectrum disorders (ASD) using agents that activate the Locus Coeruleus-Noradrenergic (LC-NA) system of the brain and to methods for screening for compounds to treat ASD.

BACKGROUND OF THE INVENTION

Throughout this application various publications are referred to in parentheses. Citations for these references may be found at the end of the specification immediately preceding the claims. The disclosures of these publications are hereby incorporated by reference in their entireties into the subject application to more fully describe the art to which the subject application pertains.

Autism spectrum disorders (ASD) include autism and other related disorders. Autism is a behaviorally defined disorder that comprises a controversial diagnostic category due to heterogeneity in symptomatology, causation, and etiology and significant variance in response to intervention (Beglinger and Smith 2001, Pelios and Lund 2001, Szatmari 2000). Autism spectrum disorders (ASD) are heritable developmental disorders characterized by impairments in social interaction, language and communication deficits and repetitive or stereotyped behaviors. Although the genetic contributions to ASD are being intensively explored (Abrahams & Geschwind 2008, Morrow et al. 2008, Sebat et al. 2007), little is known concerning the relationship of genetic, epigenetic and environmental factors to the core features or neuropathological substrate underlying ASD (Persico & Bourgeron 2006). Parent reports, clinical observations and formal studies indicate that autistic behaviors are ameliorated in some children during febrile episodes (Curran et al. 2007). The incidence of autism spectrum disorders has been estimated to be in the range of 30-60 cases per 10,000 people (Rutter 2005). There continues to be a need for treatments for autistic subjects.

SUMMARY OF THE INVENTION

The invention provides methods for treating autism spectrum disorders (ASD) that comprise administering to a subject an agent that activates the Locus Coeruleus-Noradrenergic (LC-NA) system of the brain thereby treating autism spectrum disorders (ASD) in the subject. The invention also provides methods for screening for compounds for treating ASD comprising determining whether or not the compounds activate the LC-NA system.

DETAILED DESCRIPTION OF THE INVENTION

The invention provides a method for treating an autism spectrum disorder in a subject, the method comprising administering to the subject an agent in an amount and manner effective to activate the Locus Coeruleus-Noradrenergic (LC-NA) system of the brain and thereby treat the autism spectrum disorder in the subject.

As used herein, autism spectrum disorders (ASD) include, but are not limited to, autism, Asperger syndrome, and pervasive developmental disorders not otherwise specified (PDD-NOS). Autism can be further subdivided into low-, medium- and high-functioning autism based on IQ.

As used herein, to treat autism spectrum disorders (ASD) in a subject means to ameliorate one or more sign or symptom of autism spectrum disorders (ASD), including, for example, one or more of irritability, hyperactivity, inattention, stereotypy, inappropriate speech, impaired social interaction, impaired communication, restricted interests and repetitive behavior. Repetitive behaviors can include stereotypy (apparently purposeless movement), compulsive behavior, sameness (resistance to change), ritualistic behavior, restricted behavior and self-injury.

As used herein, agents that activate the locus coeruleus-noradrenergic (LC-NA) system of the brain include, but are not limited to, adrenergic agonists, noradrenergic re-uptake inhibitors, agents that prevent or reduce degradation of noradrenaline, antagonists of pre-synaptic inhibition of noradrenergic nerve terminals, and epigenetic agents, but do not include atomoxetine, clonidine, guanfacine, lofexidine, propanolol, methylphenidate, clomipramine or desipramine.

Adrenergic receptors exist in a variety of subtypes, including alpha and beta receptors. Alpha receptors include alpha1 and alpha2 receptors, which can be further subdivided into alpha1A, alpha 1B, alpha1D, alpha2A, alpha2B and alpha2C receptors. Beta receptors include beta1, beta2 and beta3 receptors. As used herein, the agent may act selectively at one or more adrenergic receptor subtype. Noradrenaline is also known as norepinephrine, and the terms are used interchangeably in this application.

Examples of alpha1 agonists include, but are not limited to, phenylephrine, methoxamine, cirazoline and xylometazoline. Examples of alpha2 agonists include, but are not limited to, dexmedetomidine, xylazine and tizanidine. Examples of beta1 agonists include, but are not limited to, isoprenaline and dobutamine. Examples of beta2 agonists include, but are not limited to, salbutamol (albuterol), bitolterol mesylate, formoterol, isoprenaline, levalbuterol, metaproterenol, salmeterol, terbutaline, and ritodrine. Examples of beta3 agonists include, but are not limited to, L-796568 (Nisoli et al. 1996), amibegron and solabegron. Examples of adrenergic reuptake inhibitors include, but are not limited to, 3,4-methylenedioxyamphetamine, amitriptyline, amoxapine, amphetamine, benzphetamine, dextroamphetamine, dothiepin, doxepin, duloxetine, imipramine, iprindole, maprotiline, mazindol, methamphetamine, milnacipran, n-methyl-3,4-methylenedioxyamphetamine, nortriptyline, opipramol, protriptyline, reboxetine, reserpine, tetrabenazine, tomoxetine, trimipramine, tyramine and viloxazine. Preferably, the reuptake inhibitor is selective for inhibiting reuptake of noradrenaline and does not affect reuptake of other neurotransmitters such as dopamine.

Epigenetic agents are agents that modulate the level of expression of one or more genes. Preferably, the epigenetic agent is selective in modulating the level of expression of genes that activate the Locus Coeruleus-Noradrenergic (LC-NA) system of the brain.

The invention provides a method for screening for compounds for treating autism spectrum disorders (ASD), the method comprising determining whether or not the compound activates the locus coeruleus-noradrenergic (LC-NA) system of the brain, wherein activation of the LC-NA system indicates that the compound is a candidate for treating ASD and wherein lack of activation of the LC-NA system indicates that the compound is not a candidate for treating ASD. Compounds that could be screened include, but are not limited to, adrenergic agonists, noradrenergic re-uptake inhibitors, agents that prevent or reduce degradation of noradrenaline, antagonists of pre-synaptic inhibition of noradrenergic nerve terminals, epigenetic agents, and agents that are selective for modulating the expression of genes that activate the locus coeruleus-noradrenergic (LC-NA) system of the brain.

Screening assays could be conducted, for example, using an animal model that is unable to synthesize norepinephrine, which can be created by targeted disruption of the dopamine beta-hydroxylase (DBH) gene (Thomas and Palmiter, 1997). These animals exhibit motor deficits, such as swimming more slowly than their littermates and performing less well on a rapidly rotating rod test, and impaired performance of an active-avoidance task (Thomas and Palmiter, 1997).

This invention will be better understood from the Experimental Details, which follow. However, one skilled in the art will readily appreciate that the specifics discussed are merely illustrative of the invention as described more fully in the claims that follow thereafter.

Experimental Details

Introduction and Discussion
 Fever and Autism Spectrum Disorders.
 The association of fever and behavioral improvement in ASD provides clues to the pathophysiology of autistic behaviors and to therapeutic interventions. Accordingly, the dramatic fluctuations in behavioral states occurring during and after febrile episodes suggest the involvement of a pervasive neural system that can effect relatively rapid changes in the functional activity of widespread neural networks involved in the core features of ASD. The locus coeruleus-noradrenergic system (LC-NA) represents such a widespread and versatile neuromodulatory system that may be common to febrigenesis and the modulation of autistic behaviors. Intrinsic and environmental stressors acting upon a substrate of genetic and epigenetic variations during a protracted maturational window of vulnerability may developmentally dysregulate the LC-NA system. Febrile episodes ameliorate autistic behaviors by differentially modulating the LC-NA system and transiently restoring the functional integrity of its distributed neural networks primarily involved in mediating social communication, complex motor programs and instrumental behaviors.

Pyrogens can enter the hypothalamus in areas devoid of the blood-brain barrier, the Organum Vasculosum Lamina Terminalis (OVLT), or alternatively by activation of vagal afferents to the Nucleus Solitarius, which is monosynaptically linked to the Locus Coeruleus. Efferents from the preoptic anterior hypothalamic area and paraventricular nucleus descend to the lateral pontine tegmentum and synapse with LC neurons.

Locus Coeruleus.
 The locus coeruleus (LC) is a small-pigmented nucleus nestled in the rostral dorsolateral pontine tegmentum. The LC in humans consists of approximately 15,000-20,000 neurons with the most widespread axonal projections of any neurons in the brain (Foote et al. 1983). All of the norepinephrine (NE) in the cerebral cortex and hippocampus and most of the NE in other parts of the neuraxis including the cerebellum is transported by LC neurons in axons with thousands of NE-containing varicosities (Oleskevich et al. 1989). By virtue of their complex but selective patterns of innervations within and across different forebrain structures, LC-NA neurons gain access to a diverse but targeted array of interacting neural networks. For example, preferential noradrenergic innervation of selective components of the visual system promotes more global visual spatial analysis and elaboration of visuomotor responses as opposed to a greater focus on stimulus feature extraction and pattern analysis, consistent with the visual sensory domains most impaired in autism (Berridge & Waterhouse 2003). Such networks are influenced through actions at multiple stages of sensorimotor processing, co-localized neuromodulators, noradrenergic receptor subtype topography, activation of distinct intracellular signaling cascades, elaboration of a dynamic range of neuronal response properties and rapid reorganization of relevant neural networks for efficient and flexible behavioral adaptations (Berridge & Waterhouse 2003). The widespread efferent projections of the LC are paralleled by equally diverse afferent projections to LC neuron cell bodies and their dendritic systems (Van Bockstaele et al. 2001). These arise from brainstem catecholamine- and serotonin-containing nuclei that provide homeostatic inputs to modulate LC-NA output properties as well as afferents from the cerebral cortex, amygdala, basal forebrain and hypothalamus that provide integrated feedback modulation based on evolving environmental contingencies. There is also evidence for separate corticotropin-releasing hormone (CRH) inputs to the locus coeruleus that modulate noradrenergic neuronal activation by physiological and environmental stressors (Aston-Jones & Cohen 2005).

Earlier views of the preeminent role of the LC-NA system in arousal and attention have been greatly expanded to include involvement of the LC-NA system in virtually all aspects of behavioral adaptations and performance with particular relevance to integrative cognitive domains disproportionately affected in ASD: exploration within a complex and dynamic environment and the acquisition, retention, manipulation and utilization of salient environmental cues (Aston-Jones & Cohen 2005, Van Bockstaele et al. 2001). The operation of the LC-NA system in mammals has been analogized with the neuromodulatory function of neurons that regulate 'flips' in complex behavior patterns in invertebrates (Bouret & Sara 2005). The organizing principle that emerges from recent research is that distributed neural networks throughout the brain are under modulatory control by the LC-NA system and associated homeostatic signals including circadian rhythms to facilitate rapid and widespread neural network remodeling to promote behavioral adaptations to environmental imperatives. It is therefore not surprising that the LC-NA system has been implicated in the etiology of post-traumatic stress disorders, neurodegenerative diseases, schizophrenia, depression and other psychiatric conditions (Aston-Jones & Cohen 2005, Berridge 2008, Van Bockstaele et al. 2001). The role of the LC-NA system in autism has escaped attention until now.

Febrigenesis and the LC-NA System.
 What is the evidence that febrigenesis involves the LC-NA system? Bacterial lipopolysaccharide (LPS)-induced fever activates preoptic area noradrenergic terminals (Linthorst et al. 1995) and chemical lesions of NE-containing afferents to the paraventricular nucleus inhibit the fever response to interleukin-1 (Ovadia et al. 1989). While it is now well established that preoptic NE mediates LPS-induced fever (Feleder et al. 2007), the NE neurons involved in fever have only recently been elucidated in findings that electrolytic and chemical lesions of LC markedly attenuate LPS-induced fever in laboratory animals (Almeida et al. 2004). Thus reciprocally projecting LC-NA-hypothalamic pathways activated by febrigenic stimuli alter the excitatory state of LC-NA neurons during fever. Since LC neurons exhibit highly synchronized activity attributable to dendritic electrical interactions, activation of the subpopulation of LC neurons projecting to the hypothalamus could readily spread throughout the nucleus, causing functional remodeling and altered neuronal response properties of differential components of the entire LC-NA system. Altered LC-NA neural network deployment and neuronal activation may be the restorative event in the transient amelioration of autistic behaviors during fever. This is in keeping with studies that have failed to find substantive neuropathological lesions in the cerebral cortex and other brain sites (Amaral et al. 2008), and reports of the paucity of associated anatomical abnormalities in the LC in ASD (Hashemi et al. 2007, Martchek et al. 2006). Insofar as ASD is a heterogeneous disorder in which waxing and waning of autistic behaviors occurs during fever and defervescence and also during specific developmental epochs, the neural networks responsible for ASD, particularly in higher functioning patients, should be functionally intact. This has implications for a rational pharmacotherapy of autism that targets the LC-NA system and its diverse pre- and postsynaptic receptors. Although favorable responses to some alpha-adrenergic agonists have been reported in ASD (Erickson et al. 2007), the diversity of neurochemical, developmental and epigenetic regulatory systems associated with the LC-NA system (see below) suggest that more diverse, selective, versatile and novel therapeutic targets and agents could emerge.

There remains to consider the events and processes that could lead to developmental dysregulation of the LC-NA system and ASD. Intricate profiles of developmental cues are elaborated during progressive developmental critical periods to ensure the fidelity of deployment of the emerging LC-NA system (Hashemi et al. 2007, Holm et al. 2006). A significant subset of these interacting developmental genes and gene networks has been implicated in ASD (Abrahams & Geschwind 2008, Morrow et al. 2008, Schanen 2006). LC-NA developmental genes are under exquisite degrees of epigenetic regulation, suggesting the influence of complex gene-environmental interactions and high degrees of contextual control (Hashemi et al. 2007, Holm et al. 2006, Persico & Bourgeron 2006, Schanen 2006). These observations are consistent with emerging observations suggesting the dysregulation of multiple epigenetic regulatory processes in ASD (Persico & Bourgeron 2006, Schanen 2006). ASD-associated epigenetic alterations in the fidelity of regional patterning, specification and progressive maturation of the LC-NA system and its widely distributed afferent and efferent connections would result in a complex amalgam of core behavioral deficits and a spectrum of clinical severity depending on the profile of maturational deficits associated with epigenetic dysregulation of specific developmental critical periods (Aston-Jones & Cohen 2005, Berridge & Waterhouse 2003, Bouret & Sara 2005, Hashemi et al. 2007, Holm et al. 2006, Persico & Bourgeron 2006, Schanen 2006).

Prenatal stressors, appropriately timed and sufficiently intense, could also be important in dysregulating the LC-NA system. In view of the metabolic load LC neurons bear in supporting vast axonal networks with millions of NE laden vesicles, they might be selectively vulnerable to stress-induced functional dysregulation. Prenatal stressful events are reported more frequently in mothers of autistic children than mothers of control children (Beversdorf, 2005). Natural disasters are compelling in this respect. These have revealed a significant increase in autism prevalence following maternal exposure to hurricanes and tropical storms over a 15-year period in Louisiana (Kinney et al. 2008). A dose-response effect was related to the severity of storm exposure. Interestingly, maternal exposure to severe storms at mid-gestation resulted in the highest prevalence of autism in affected cohorts.

To the extent that high levels of maternal stress-induced cortisol might affect fetal LC-NA regulation, it is of interest that at mid-gestation the catalytic enzyme that inactivates cortisol, 11 β-hydroxysteroid dehydrogenase-2, is downregulated in the placenta, thereby enhancing transplacental transport of the stress hormone into the fetal brain (Holmes, et al. 2006). In addition, during this critical period for progressive phases of locus coeruleus development, 11 β-hydroxysteroid dehydrogenase-2 is under dynamic and potentially deregulated epigenetic modulation through the actions of differential promoter CpG island methylation, methyl CpG-binding proteins and specific transcriptional regulators associated with ASD (Abrahams & Geschwind 2008, Moriceau & Sullivan 2005). These intrauterine perturbations can significantly alter the normal neuronal and regional noradrenergic receptor subunit complement, electrotonic coupling and associated early attachment learning and environmental discrimination (Moriceau & Sullivan 2005). Interestingly, Crh gene expression is elevated in a Rett syndrome (MeCP2 mutant) mouse model and is associated with abnormal stress responses (McGill et al. 2006). MeCP2 is known to bind the Crh promoter that is normally enriched in methylated CpG dinucleotides, and exogenous NE administration ameliorates the abnormal neural response networks observed in MeCP2 mutant mice (McGill et al. 2006, Viemari et al. 2005). These observations suggest that in addition to intrinsic epigenetically mediated ASD developmental abnormalities occurring during progressive stages of locus coeruleus development and system-wide neural network deployment, there are concurrent and continuing epigenetically dependent environmental stressors that have the potential to further compromise the functional integrity of LC-NA neural networks.

In summary, children with autism spectrum disorders (ASD) exhibit improved behaviors and enhanced communication during febrile episodes. Febrigenesis and the behavioral-state changes associated with fever in autism are hypothesized to depend upon selective normalization of key components of a functionally impaired locus coeruleus-noradrenergic (LC-NA) system. Autistic behaviors are posited to result from developmental dysregulation of LC-NA system specification and neural network deployment and modulation linked to the core behavioral features of autism. Fever transiently restores the modulatory functions of the LC-NA system and amelioration of autistic behaviors. Fever-induced reversibility of autism suggests preserved functional integrity of widespread neural networks subserving the LC-NA system and specifically the subsystems involved in mediating the cognitive and behavioral repertoires compromised in ASD. Alterations of complex gene-environmental interactions and associated epigenetic mechanisms during seminal developmental critical periods are viewed as instrumental in LC-NA dysregulation as emphasized by the timing and severity of prenatal maternal stressors on autism prevalence. This hypothesis has implications for a rational approach to designing therapeutic agents for ASD that target the LC-NA system's diverse network of pre- and postsynaptic receptors, intracellular signaling pathways and dynamic epigenetic remodeling processes involved in their regulation and functional plasticity. The association of febrile episodes and improvement in autistic behaviors provides a basis for the use of alpha adrenergic agonists and alpha adrenergic re-uptake inhibitors for the treatment of autism.

REFERENCES

Abrahams, B. S. & Geschwind, D. H. Advances in autism genetics: on the threshold of a new neurobiology. Nat Rev Genet 9, 341-55 (2008).

Alikhani-Koopaei, R., Fouladkou, F., Frey, F. J. & Frey, B. M. Epigenetic regulation of 11 beta-hydroxysteroid dehydrogenase type 2 expression. J Clin Invest 114, 1146-57 (2004).

Almeida, M. C., Steiner, A. A., Coimbra, N. C. & Branco, L. G. Thermoeffector neuronal pathways in fever: a study in rats showing a new role of the locus coeruleus. J Physiol 558, 283-94 (2004).

Amaral, D. G., Schumann, C. M. & Nordahl, C. W. Neuroanatomy of autism. Trends Neurosci 31, 137-45 (2008).

Aston-Jones, G. & Cohen, J. D. An integrative theory of locus coeruleus-norepinephrine function: adaptive gain and optimal performance. Annu Rev Neurosci 28, 403-50 (2005).

Beglinger L J, Smith T H. A review of subtyping in autism and proposed dimensional classification model. J Autism Dev Disord. 2001 August; 31(4):411-22.

Berridge, C. W. Noradrenergic modulation of arousal. Brain Res Rev 58, 1-17 (2008).

Berridge, C. W. & Waterhouse, B. D. The locus coeruleus-noradrenergic system: modulation of behavioral state and state-dependent cognitive processes. Brain Res Rev 42, 33-84 (2003).

Beversdorf, D. Q. et al. Timing of prenatal stressors and autism. J Autism Dev Disord 35, 471-8 (2005).

Bouret, S. & Sara, S. J. Network reset: a simplified overarching theory of locus coeruleus noradrenaline function. Trends Neurosci 28, 574-82 (2005).

Curran, L. K. et al. Behaviors associated with fever in children with autism spectrum disorders. Pediatrics 120, e1386-92 (2007).

Erickson, C. A., Posey, D. J., Stigler, K. A. & McDougle, C. J. Pharmacologic treatment of autism and related disorders. Pediatr Ann 36, 575-85 (2007).

Feleder, C., Perlik, V. & Blatteis, C. M. Preoptic norepinephrine mediates the febrile response of guinea pigs to lipopolysaccharide. Am J Physiol Regul Integr Comp Physiol 293, R1135-43 (2007).

Foote, S. L., Bloom, F. E. & Aston-Jones, G. Nucleus locus ceruleus: new evidence of anatomical and physiological specificity. Physiol Rev 63, 844-914 (1983).

Hashemi, E., Sahbaie, P., Davies, M. F., Clark, J. D. & DeLorey, T. M. Gabrb3 gene deficient mice exhibit increased risk assessment behavior, hypotonia and expansion of the plexus of locus coeruleus dendrites. Brain Res 1129, 191-9 (2007).

Holm, P. C. et al. BMPs, FGF8 and Wnts regulate the differentiation of locus coeruleus noradrenergic neuronal precursors. J Neurochem 99, 343-52 (2006).

Holmes, M. C. et al. The mother or the fetus? 11beta-hydroxysteroid dehydrogenase type 2 null mice provide evidence for direct fetal programming of behavior by endogenous glucocorticoids. J Neurosci 26, 3840-4 (2006).

Kinney, D. K., Miller, A. M., Crowley, D. J., Huang, E. & Gerber, E. Autism prevalence following prenatal exposure to hurricanes and tropical storms in Louisiana. J Autism Dev Disord 38, 481-8 (2008).

Linthorst, A. C., Flachskamm, C., Holsboer, F. & Reul, J. M. Intraperitoneal administration of bacterial endotoxin enhances noradrenergic neurotransmission in the rat preoptic area: relationship with body temperature and hypothalamic-pituitary-adrenocortical axis activity. Eur J Neurosci 7, 2418-30 (1995).

Martchek, M., Thevarkunnel, S., Bauman, M., Blatt, G. & Kemper, T. Lack of evidence of neuropathology in the locus coeruleus in autism. Acta Neuropathol 111, 497-9 (2006).

McGill, B. E. et al. Enhanced anxiety and stress-induced corticosterone release are associated with increased Crh expression in a mouse model of Rett syndrome. Proc Natl Acad Sci U S A 103, 18267-72 (2006).

Moriceau, S. & Sullivan, R. M. Neurobiology of infant attachment. Dev Psychobiol 47, 230-42 (2005).

Morrow, E. M. et al. Identifying autism loci and genes by tracing recent shared ancestry. Science 321, 218-23 (2008).

Nisoli E, Tonello C, Landi M, Carruba M O (1996). Functional studies of the first selective $\beta_3$-adrenergic receptor antagonist SR 59230A in rat brown adipocytes. Mol. Pharmacol. 49 (1): 7-14.

Oleskevich, S., Descarries, L. & Lacaille, J. C. Quantified distribution of the noradrenaline innervation in the hippocampus of adult rat. J Neurosci 9, 3803-15 (1989).

Ovadia, H., Abramsky, O. & Weidenfeld, J. Evidence for the involvement of the central adrenergic system in the febrile response induced by interleukin-1 in rats. J Neuroimmunol 25, 109-16 (1989).

Pelios L V, Lund S K. A selective overview of issues on classification, causation, and early intensive behavioral intervention for autism. Behav Modif. 2001 October; 25(5):678-97.

Persico, A. M. & Bourgeron, T. Searching for ways out of the autism maze: genetic, epigenetic and environmental clues. Trends Neurosci 29, 349-58 (2006).

Rutter M. Incidence of autism spectrum disorders: changes over time and their meaning. Acta Paediatr. 2005 January; 94(1):2-15.

Schanen, N. C. Epigenetics of autism spectrum disorders. Hum Mol Genet 15 Spec No 2, R138-50 (2006).

Sebat, J. et al. Strong association of de novo copy number mutations with autism. Science 316, 445-9 (2007).

Szatmari P. The classification of autism, Asperger's syndrome, and pervasive developmental disorder. Can J Psychiatry. 2000 October; 45(8):731-8.

Thomas S A, Palmiter R D. Disruption of the dopamine beta-hydroxylase gene in mice suggests roles for norepinephrine in motor function, learning, and memory. Behav. Neurosci. 1997 June; 111 (3):579-89.

Van Bockstaele, E. J., Bajic, D., Proudfit, H. & Valentino, R. J. Topographic architecture of stress-related pathways targeting the noradrenergic locus coeruleus. Physiol Behav 73, 273-83 (2001).

Viemari, J. C. et al. Mecp2 deficiency disrupts norepinephrine and respiratory systems in mice. J Neurosci 25, 11521-30 (2005).

What is claimed is:

1. A method for screening for compounds for treating autism spectrum disorders (ASD), the method comprising determining whether or not the compound activates the locus coeruleus-noradrenergic (LC-NA) system of the brain, wherein activation of the LC-NA system indicates that the compound is a candidate for treating ASD and wherein lack of activation of the LC-NA system indicates that the compound is not a candidate for treating ASD, and wherein screening is conducted by administering the compound to an animal model that is unable to synthesize norepinephrine and that exhibits a motor deficit and/or impaired performance of an active-avoidance task, wherein improvement of the motor deficit and/or performance of the active-avoidance task following administration of the compound is indicative that the compound activates the LC-NA system.

2. The method of claim 1, wherein the autism spectrum disorder is autism.

3. The method of claim 1, wherein the agent is an adrenergic agonist.

4. The method of claim 3, wherein the agonist is selective for one or more adrenergic receptor subtype.

5. The method of claim 1, wherein the agent is a noradrenergic re-uptake inhibitor.

6. The method of claim 1, wherein the agent is an antagonist of pre-synaptic inhibition of noradrenergic nerve terminals.

* * * * *